United States Patent [19]
Toth et al.

[11] Patent Number: 5,644,614
[45] Date of Patent: Jul. 1, 1997

[54] COLLIMATOR FOR REDUCING PATIENT X-RAY DOSE

[75] Inventors: Thomas Louis Toth, Brookfield; Willi Walter Hampel, St. Francis, both of Wis.

[73] Assignee: General Electric Company, Milwaukee, Wis.

[21] Appl. No.: 576,152

[22] Filed: Dec. 21, 1995

[51] Int. Cl.$^6$ .................................................. G21K 1/02
[52] U.S. Cl. .......................... 378/147; 378/4; 378/145
[58] Field of Search ........................ 378/4, 147, 145, 378/148, 149, 150, 152, 159, 160

[56] References Cited

U.S. PATENT DOCUMENTS

| | | | |
|---|---|---|---|
| 4,975,933 | 12/1990 | Hampel | 378/5 |
| 4,991,189 | 2/1991 | Boomgaarden et al. | 378/4 |
| 5,054,041 | 10/1991 | Hampel | 378/4 |
| 5,231,654 | 7/1993 | Kwasnick et al. | 378/145 |
| 5,231,655 | 7/1993 | Wei et al. | 378/147 |
| 5,293,417 | 3/1994 | Wei et al. | 378/147 |
| 5,377,252 | 12/1994 | Liebetruth | 378/147 |
| 5,493,599 | 2/1996 | Mattson | 378/147 |

OTHER PUBLICATIONS

Crawford et al., "Computed tomography scanning with simultaneous patient translation", *Medical Physics*, vol. 17, No. 6, Nov./Dec. 1990, pp. 967–982.

*Primary Examiner*—Don Wong
*Attorney, Agent, or Firm*—John S. Beulick; John H. Pilarski

[57] ABSTRACT

The present invention, in one form, is a pre-patient collimator for reducing patient x-ray dose during a scan with a computed tomography system. The collimator has a contoured aperture for emitting a generally rectangular shaped x-ray fan beam. The fan beam approximates the rectangular shape of x-ray detectors which gather data for producing an image.

17 Claims, 3 Drawing Sheets

COLLIMATOR FOR REDUCING PATIENT X-RAY DOSE

FIELD OF THE INVENTION

This invention relates generally to computed tomography (CT) imaging and more particularly to collimating x-ray beams to reduce patient x-ray dose.

BACKGROUND OF THE INVENTION

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The detectors are generally rectangular. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector. In an axial scan, the projection data is processed to construct an image that corresponds to a two dimensional slice taken through the object. Typically, the configuration of a slice may be varied. One method for reconstructing an image from a set of projection data is referred to in the art as the filtered back projection technique. This process converts that attenuation measurements from a scan into integers called "CT numbers" or "Hounsfield units", which are used to control the brightness of a corresponding pixel on a cathode ray tube display.

The x-ray source typically includes an evacuated x-ray envelope containing an anode and a cathode. X-rays are produced when electrons from the cathode are accelerated against a focal spot on the anode by applying a high voltage across the anode and cathode. The x-rays diverge from the focal spot in a generally conical pattern.

In known CT systems, the x-ray beam from the x-ray source is projected through a pre-patient collimating device, or collimator, that defines the x-ray beam profile in the patient axis, or z-axis. The collimator includes x-ray absorbing material with an aperture therein for restricting the x-ray beam. The process of restricting the x-ray beam to the desired fan beam profile is termed "collimation".

With respect to restricting the x-ray beam, known collimators typically include two opposing metallic blades that may be opened and closed to change the aperture width. The fan beam "thickness", as measured along the z-axis, can be selected by adjusting the blade orientation. The blades also may be moved in a same direction to displace the centerline of the aperture. Changing the aperture centerline changes the fan beam angle with respect to the z-axis. Known apertures are typically linear, or rectangular.

The collimated beam attenuates through a patient and the attenuated beam at least partially falls on a detector array. Known detector arrays typically include detector cells arranged in an arc configuration having a constant radius from the source. Since the collimator aperture is rectangular, an effective source to collimation distance (s) changes as the fan angle ($\alpha$) at which the fan beam impinges upon the detector cells of the detector array changes. Therefore, a convex shaped collimated x-ray beam is projected on the detector. However, when a post-patient collimator is used, each detector cell typically senses only a rectangular portion of the x-ray beam umbra. A portion of the convex shaped attenuated x-ray beam is not used. A patient, therefore, is subject to unnecessary x-ray dose since a portion of the attenuated beam is unused. To reduce unnecessary x-ray dose, the collimator aperture can be narrowed. Narrowing the collimator aperture, however, also reduces the data collected by the detector.

In multislice CT systems, it is desirable to have only the umbra of the x-ray beam fall on the detector cells. Although the x-ray beam can initially be collimated so that the penumbra does not fall on the detector cells, thermal expansion of the anode support structure as the x-ray source heats up affects the alignment of the fan beam with the imaging plane. Gravitational and centrifugal forces are also known to cause focal spot movement, which also results in fan beam movement. As the fan beam moves, it is possible that at least part of the penumbra will fall on the detector cells. Movement of the fan beam changes the strength of signals from the detector array cells. Such fan beam movement may cause differential gain errors and result in severe ring, band and center artifacts unless sophisticated signal correction is employed. However, even when using perfect closed loop beam stabilization to minimize the beam movement on the detector, i.e., moving the detector or collimator, the convex beam shape results in subjecting the patient to some amount of unnecessary x-ray dose.

It would be desirable to restrict the fan beam to reduce the unnecessary x-ray dose while maintaining the amount and quality of data currently collected by detector cells. It also would be desirable to restrict the beam to more closely approximate the shape of each detector element in multislice CT systems which depend upon distinguishing between the umbra and penumbra of the fan beam.

SUMMARY OF THE INVENTION

These and other objects may be attained by a collimator which, in one embodiment, has a contoured aperture. Particularly, the collimator aperture is contoured so that the x-ray beam emitted from the collimator has a generally rectangular shape on the detector. The generally rectangular shaped beam can be sized, e.g., by adjusting the collimator aperture width, to approximate the size of a detector cell so that the area of beam not impinging on such cell is reduced compared to a convex beam. Unnecessary patient dose is thus decreased and the detector data is maintained. The rectangular beam on the detector is also believed to improve the performance of multislice systems.

The collimator described above restricts the fan beam to more approximate the size of each detector cell. Moreover, the collimator reduces unnecessary patient exposure to x-ray dose. Furthermore, the collimator does not decrease the amount or quality of image data received by each detector cell.

DETAILED DESCRIPTION OF THE DRAWINGS

Figure 1:
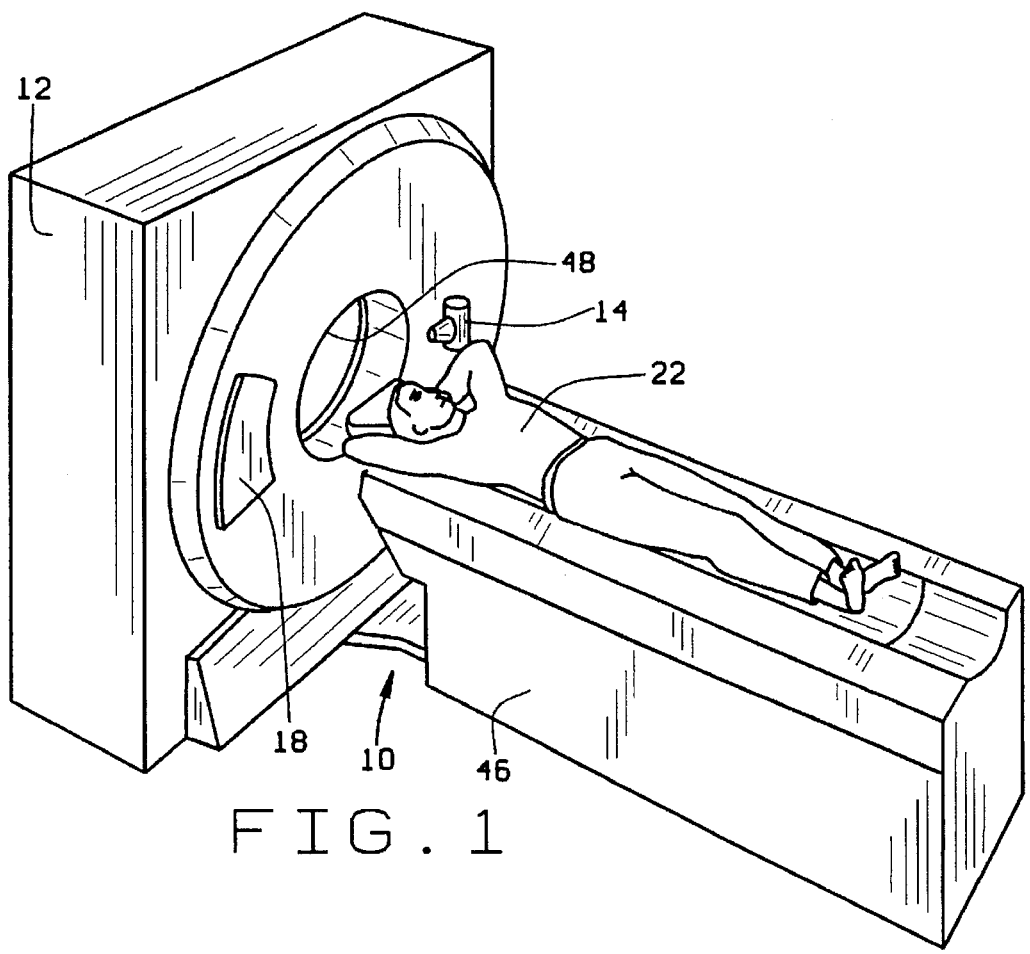
FIG. 1 is a pictorial view of a CT imaging system.
Figure 2:
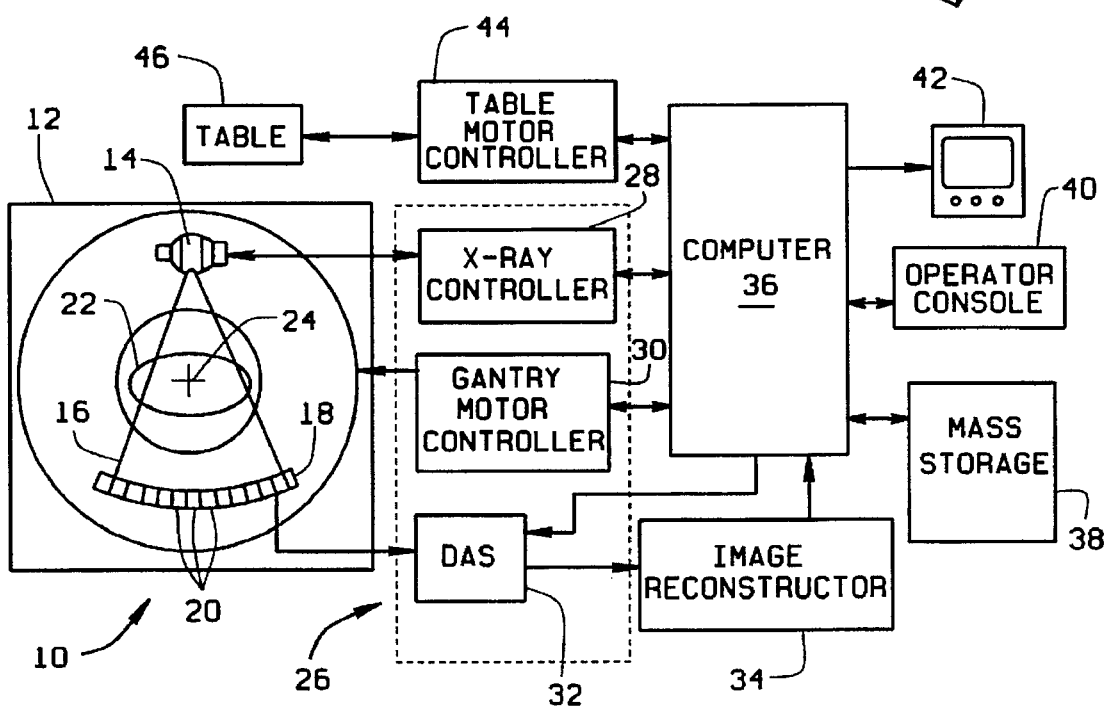
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a fan beam of x-rays 16 toward a detector array 18 on the opposite side of gantry 12. Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
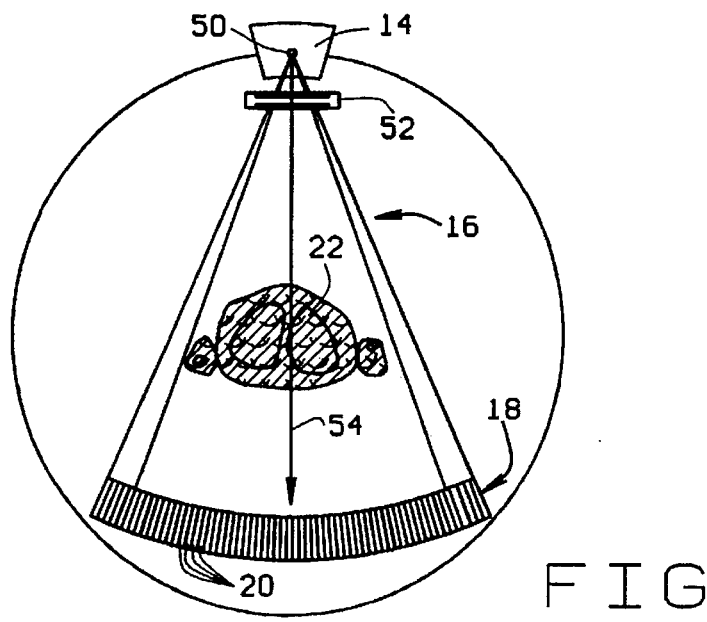
FIG. 3 is a schematic view of a CT imaging system with a collimator.

Referring to FIG. 3, and with respect to operation of x-ray source 14, x-ray beam 16 emanates from a focal spot 50 of source 14. X-ray beam 16 is collimated by collimator 52, and collimated beam 16 is projected toward detector array 18 along a fan beam axis 54 centered within fan beam 16.

Figure 4:
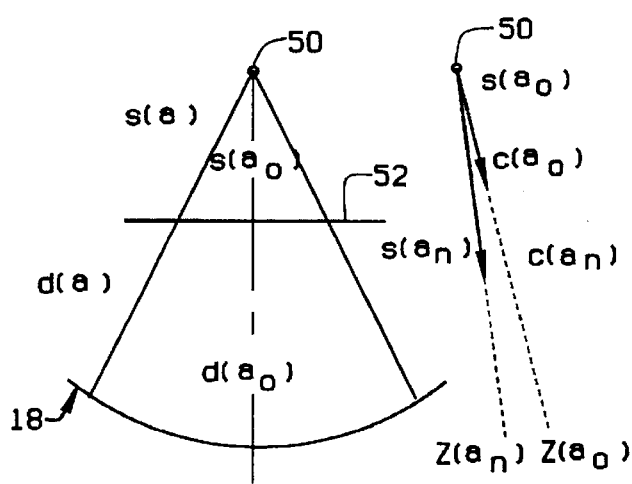
FIG. 4 is a schematic view of a fan beam, a collimator and a detector.

As shown in FIG. 4, detector array 18 is generally curved at a fixed radius from focal point 50. A distance (d) between focal spot 50 and the center of any detector element 20 at a fan beam angle ($\alpha$) is the same. Particularly:

$$d(\alpha_o) = d(\alpha_n)$$

where:

$\alpha_o$=fan beam angle at vertical; and $\alpha_n$=fan beam angle at any angle offset to vertical.

As described above, known collimators have rectangular, or linear, apertures, or slots. A distance (s) between x-ray source 14 and the collimator aperture changes as a function of fan beam angle ($\alpha$). Particularly:

$$s(\alpha_o) < s(\alpha_n)$$

where:

$\alpha_o$=is the fan beam angle at vertical; and $\alpha_n$=fan beam angle at any angle offset to vertical.

Figure 5:
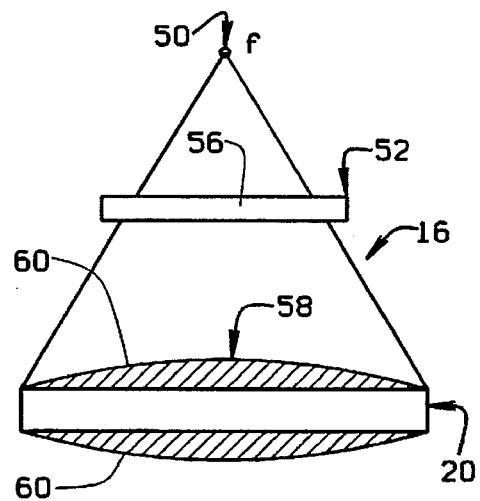
FIG. 5 is a schematic view of a known collimator aperture and a convex beam.

As shown in FIG. 5, collimated fan beam 16 collimated by collimator 52 with a rectangular slot or aperture 56 is generally convex as indicated at 58. Particularly, each x-ray in beam 16 impinges upon detector cells 20 in detector array 18 at a z axis location, $Z(\alpha)$, according to the equation:

$$Z(\alpha) = (c-f)d(\alpha)/s(\alpha) + f$$

where:

$\alpha$=fan beam angle;

Z=position of beam on detector;

f=position of focal spot in z axis;

c=position of collimation point in z axis;

d=source to detector distance; and s=source to collimation distance.

However, since detector elements 20 are generally rectangular, portions of convex fan beam 16 do not impinge detector elements 20. This unused portion 60 (shaded), however, has been attenuated by patient 22. Patient 22 was thus unnecessarily subjected to the full convex fan beam.

Figure 6:
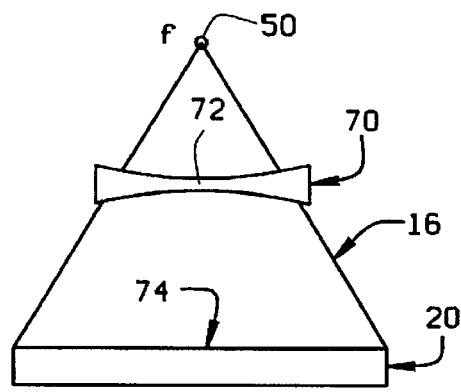
FIG. 6 is a schematic view of a collimator aperture in accordance with one embodiment of the present invention.

Referring to FIG. 6, and in accordance with one embodiment of the present invention, a collimator 70 has a contoured aperture 72 therein. Contoured aperture 72 is curved and receives x-ray beams from x-ray source and emits a generally rectangular beam 74 which impinges upon detector elements 20 in detector array 18. As shown, rectangular beam 74 directly overlaps the rectangular detector element 20. Therefore, in one embodiment, contoured aperture 72 prevents any unused portions of fan-beam 16 from impinging on detector elements 20, and thus eliminates patient exposure to unnecessary x-ray dose.

In accordance with another embodiment of the present invention, a collimator aperture is curved according to the following equation:

$$c(\alpha) = (Z-f)s(\alpha)/d(\alpha) + f$$

where:

$\alpha$=fan beam angle;

Z=position of beam on detector;

f=position of focal spot in z axis;

c=position of collimation point in z axis;

d=source to detector distance; and s=source to collimation distance.

In accordance with yet another embodiment of the present invention a collimator aperture is contoured for each slice configuration and focal spot size. For example, a cam collimator, as hereinafter described in more detail, may be used to continuously change aperture shape as a function of the aperture size.

Figure 7:
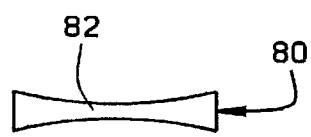
FIG. 7 is a schematic view of a collimator aperture in accordance with another embodiment of the present invention.

In accordance with still yet another embodiment of the invention, as shown in FIG. 7, collimator 80 has a collimator aperture 82 that is contoured with a fixed linear ramp. The fixed linear ramp approximates the curvature for a nominal slice configuration. For example, where a distance between x-ray source 14 and patient 22 is 541 mm, a distance between x-ray source 14 and detector element 20 is 949 mm, and a vertical distance between x-ray source 14 and collimator is 162 mm, a ramp slope of 0.2 mm per 100 mm may be used. Linear ramp aperture 82 provides similar patient dose savings and is believed to be easier to manufacture than multiple curved or linear contours.

Figure 8:
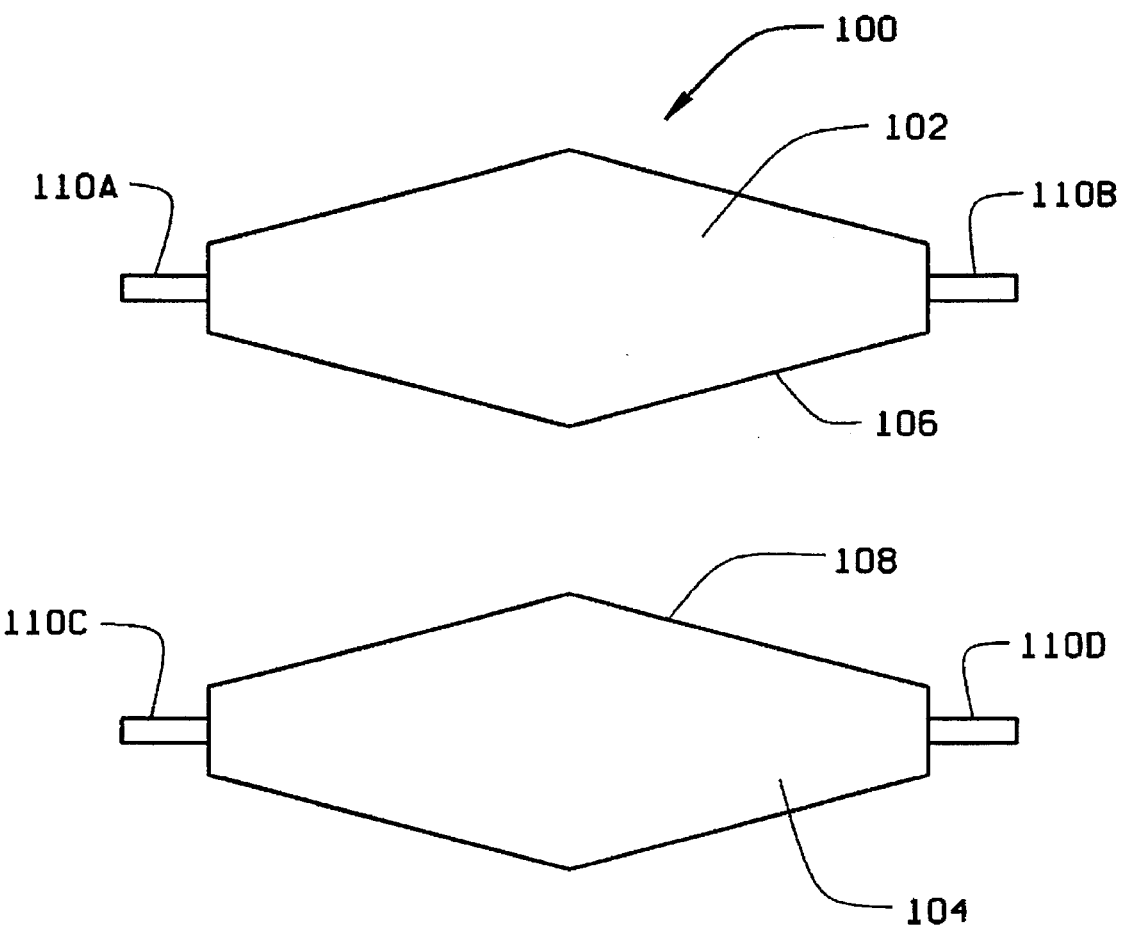
FIG. 8 is a top view of a double cam collimator in accordance with yet another embodiment of the present invention.

FIG. 8 is a top view of a double cam collimator 100 in accordance with yet another embodiment of the present invention. Collimator 100 includes cams 102 and 104. Cams 102 and 104 are shown as being spaced and generally define edges 106 and 108, respectively, for restricting a beam passing therebetween. Cams 102 and 104 each include bosses 110A, 110B, 110C and 110D extending therefrom. A stepper motor (not shown) would be coupled to at least one boss 110A,110B and 110C,110D of each cam 102 and 104 to control relative movement of such cams 102 and 104.

The collimators with contoured apertures as described above restrict collimated fan beam 16 to more closely approximate the size of detector cells 20. By so restricting collimated fan beam 16, unused portions of x-ray beams attenuated by patient 22 are reduced, yet the integrity of data received at detector cells 20 is maintained.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used. Moreover, the linear ramp contoured aperture described herein has a ramp slope of 0.2 mm per 100 mm. Many other ramp slopes can be used. Furthermore, the aperture contour may be prefabricated with a specific curvature or slope or, alternatively, the aperture contour may be modified during a scan. Accordingly, the spirit and scope of the invention are to be limited only by the terms of the appended claims.

What is claimed is:

1. A pre-patient collimator for controlling the shape of a collimated fan beam for use in a computed tomography system, the computed tomography system including a detector array having a plurality of rectangular shaped detector cells and an x-ray source, said collimator comprising x-ray absorbing material having an aperture therein for restricting the collimated fan beam, said aperture contour providing that a fan beam umbra of a beam passing therethrough has a substantially rectangular cross sectional shape.

2. A pre-patient collimator in accordance with claim 1 wherein the system is configured to scan an object, and wherein the dimensions of said contoured aperture may change contour.

3. A pre-patient collimator in accordance with claim 1 wherein said aperture is contoured with a fixed linear ramp.

4. A pre-patient collimator in accordance with claim 3 wherein said fixed linear ramp has a ramp slope of 0.2 mm per 100 mm.

5. A pre-patient collimator in accordance with claim 1 wherein the detector array comprises at least one generally rectangular detector element, and wherein said aperture is contoured so that a fan beam umbra of a beam passing therethrough is substantially fitted to the rectangular detector element.

6. A pre-patient collimator in accordance with claim 1 wherein said collimator is a double cam collimator comprising a first cam and a second cam, at least said first cams being movable relative to said second cam.

7. A pre-patient collimator in accordance with claim 1 wherein said collimator aperture can be adjusted as a function of a focal spot size of the x-ray source.

8. A pre-patient collimator in accordance with claim 1 wherein the system is configured to reconstruct slices of varying configurations, and wherein said aperture is contoured as a function of the slice configuration.

9. A pre-patient collimator for controlling the shape of a collimated fan beam for use in a computed tomography system, the computed tomography system including a detector array and an x-ray source, said collimator comprising x-ray absorbing material having an aperture therein for restricting the collimated fan beam, said aperture having a contour substantially according to:

$$c(\alpha) = (Z-f)s(\alpha)/d(\alpha) + f$$

where:

$\alpha$ = fan beam angle;

$Z$ = position of beam on detector;

$f$ = position of focal spot in z axis;

$c$ = position of collimation point in z axis;

$d$ = source to detector distance; and $s$ = source to collimation distance.

10. In an imaging system including an x-ray source and a detector array having a plurality of rectangular shaped x-ray detector cells, a collimator comprising x-ray absorbing material having an aperture therein for restricting the collimated fan beam, said aperture having a contour to form a generally rectangular collimated fan beam and said aperture contour providing that a fan beam umbra of a beam passing therethrough is substantially fitted to the rectangular detector cells.

11. A collimator in accordance with claim 10 wherein said aperture is contoured according to:

$$c(\alpha) = (Z-f)s(\alpha)/d(\alpha) + f$$

where:

$\alpha$ = fan beam angle;

$Z$ = position of beam on detector;

$f$ = position of focal spot in z axis;

$c$ = position of collimation point in z axis;

$d$ = source to detector distance; and $s$ = source to collimation distance.

12. A collimator in accordance with claim 10 wherein said aperture is contoured with a fixed linear ramp.

13. A collimator in accordance with claim 12 wherein said fixed linear ramp has a ramp slope of 0.2 mm per 100 mm.

14. A collimator in accordance with claim 10 wherein the system is configured to scan an object, and wherein the dimensions of said contoured aperture are adjustable.

15. A collimator in accordance with claim 10 wherein said collimator is a cam collimator.

16. A collimator in accordance with claim 10 wherein said collimator aperture can be adjusted as a function of a focal spot size of the x-ray source.

17. A collimator in accordance with claim 10 wherein the system is configured to reconstruct slices of varying configurations, and wherein said aperture is contoured as a function of the slice configuration.

* * * * *